US009883941B2

(12) United States Patent
Hastings et al.

(10) Patent No.: US 9,883,941 B2
(45) Date of Patent: Feb. 6, 2018

(54) REPLACEMENT HEART VALVE

(71) Applicant: Boston Scientific Scimed, Inc., Maple Grove, MN (US)

(72) Inventors: Roger N. Hastings, Maple Grove, MN (US); Mark L. Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 614 days.

(21) Appl. No.: 13/920,847

(22) Filed: Jun. 18, 2013

(65) Prior Publication Data

US 2013/0338766 A1    Dec. 19, 2013

Related U.S. Application Data

(60) Provisional application No. 61/661,586, filed on Jun. 19, 2012.

(51) Int. Cl.
*A61F 2/24* (2006.01)

(52) U.S. Cl.
CPC .......... *A61F 2/2418* (2013.01); *A61F 2/2412* (2013.01); *A61F 2230/0006* (2013.01); *A61F 2230/0008* (2013.01); *A61F 2250/0018* (2013.01); *A61F 2250/0036* (2013.01); *A61F 2250/0039* (2013.01); *A61F 2250/0048* (2013.01)

(58) Field of Classification Search
USPC ....................... 623/2.17–2.19, 2.1, 1.24, 1.26
See application file for complete search history.

(56) References Cited

U.S. PATENT DOCUMENTS

| | | | |
|---|---|---|---|
| 5,147,391 A * | 9/1992 | Lane | 623/2.18 |
| 2004/0186558 A1 | 9/2004 | Pavcnik et al. | |
| 2005/0065597 A1 | 3/2005 | Lansac | |
| 2005/0203617 A1 | 9/2005 | Forster et al. | |
| 2007/0067021 A1 | 3/2007 | Haverkost et al. | |
| 2009/0041978 A1 | 2/2009 | Sogard et al. | |

(Continued)

FOREIGN PATENT DOCUMENTS

| | | |
|---|---|---|
| WO | 2006086135 | 8/2006 |
| WO | 2006086135 A2 | 8/2006 |

(Continued)

OTHER PUBLICATIONS

Notification of Transmittal of the International Search Report and the Written Opinion of the International Search Authority, or the Declaration for PCT/US2013/46571, dated Feb. 3, 2014.

(Continued)

*Primary Examiner* — Leslie Lopez
(74) *Attorney, Agent, or Firm* — Seager, Tufte & Wickhem LLP

(57) ABSTRACT

A replacement heart valve assembly has a stent frame and a replacement valve. The replacement valve has a plurality of leaflets and a valve frame. The leaflets are attached to the valve frame. Further, the assembly has a plurality of suspension struts attached to the stent frame and the valve frame. The valve frame is suspended within the stent frame via the suspension struts. In some embodiments, the assembly further has a sealing member attached to the stent frame to prevent leakage around the replacement heart valve assembly.

7 Claims, 3 Drawing Sheets

(56) References Cited

U.S. PATENT DOCUMENTS

| | | |
|---|---|---|
| 2009/0062907 A1* | 3/2009 | Quijano et al. ............ 623/1.24 |
| 2009/0117334 A1 | 5/2009 | Sogard et al. |
| 2010/0049313 A1 | 2/2010 | Alon et al. |
| 2010/0256723 A1 | 10/2010 | Murray |
| 2011/0060576 A1 | 3/2011 | Sharma et al. |
| 2011/0098800 A1 | 4/2011 | Braido et al. |

FOREIGN PATENT DOCUMENTS

| | | |
|---|---|---|
| WO | 2006127412 | 11/2006 |
| WO | 2006127412 A1 | 11/2006 |
| WO | 2008100599 | 8/2008 |
| WO | 2008100599 A1 | 8/2008 |
| WO | 2010079426 | 7/2010 |
| WO | 2010079426 A1 | 7/2010 |

OTHER PUBLICATIONS

Invitation to Pay Additional Fees and, Where Applicable, Protest Fee, PCT Application No. PCT/US13/46571, dated Sep. 19, 2013.
Ward, C., Clinical significance of the bicuspid aortic valve. Heart, 83, pp. 81-85 (2000).
Yener, et al., Bicuspid Aortic Valve, Ann Thorac Cardiovasc Surg, vol. 8, No. 5, pp. 264-267 (2002).

\* cited by examiner

REPLACEMENT HEART VALVE

CROSS-REFERENCE TO RELATED APPLICATIONS

This Application claims the benefit of and priority to U.S. Provisional Application No. 61/661,586, filed Jun. 19, 2012, the entire contents of which are herein incorporated by reference.

STATEMENT REGARDING FEDERALLY SPONSORED RESEARCH

Not Applicable.

BACKGROUND OF THE INVENTION

It is known that heart valve insufficiency, stenosis, and defects can result in mortality of a patient. Heretofore, a variety of methods and devices have been designed to allay such conditions. One particular option is to use a replacement heart valve. Moreover, various types of replacement heart valves are implanted via minimally invasive techniques, for example transcatheter implantation.

One particular type of congenital defect is a bicuspid aortic valve. Bicuspid aortic valves are present in approximately 1%-2% of the general population and can lead to additional heart complications. C. Ward, *Clinical Significance of the Bicuspid Aortic Valve*, 83 Heart 81, 82 (2000). For example, approximately 50% of adults affected by severe aortic stenosis have a bicuspid aortic valve. Id.

In addition, while existing technologies offer some solutions for patients suffering from stenosis and/or valve insufficiency, these existing technologies suffer from a number of problems in bicuspid aortic valve applications. In particular, existing transcatheter valve replacement technologies have difficulty with bicuspid valves since the geometry of the existing valve tends to force the replacement valve out of round. This leads to increased stress within the replacement valve, reduced coaptation, and, consequently, reduced valve life. Therefore, there is a need for effective treatment options for individuals having congenital bicuspid valves or valves that have begun to function like bicuspid valves due to plaque build-up on the valve.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In some embodiments, a replacement heart valve assembly comprises a stent frame and a replacement heart valve. In some embodiments, the replacement valve has a plurality of leaflets and a valve frame. The valve leaflets are attached to the valve frame. In some embodiments, the assembly further comprises a plurality of suspension struts attached to the stent frame and the valve frame. In some embodiments, the valve frame is suspended within the stent frame via the suspension struts. In some embodiments, the assembly further comprises a sealing member and the sealing member is attached to the stent frame. In some embodiments, the sealing member is configured to prevent perivalvular leaks.

BRIEF DESCRIPTION OF THE SEVERAL VIEWS OF THE DRAWING(S)

DETAILED DESCRIPTION OF THE INVENTION

Figure 1A:
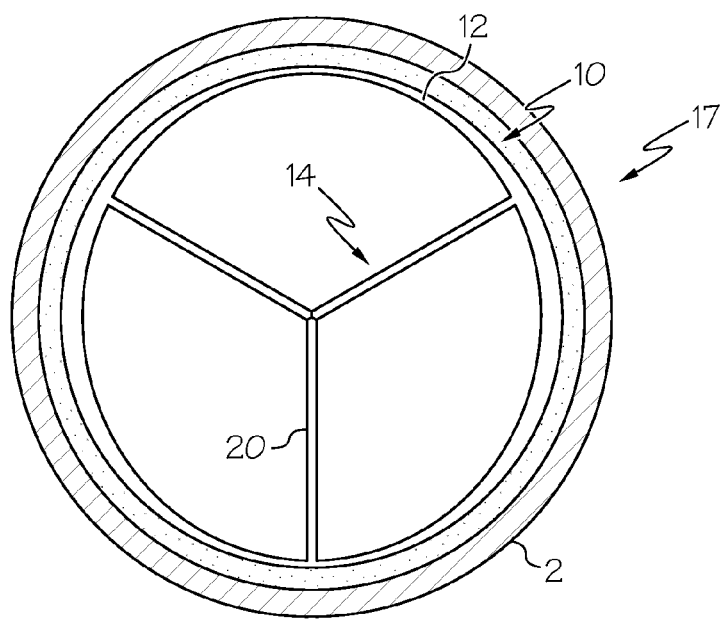
FIG. 1A shows a top view of a replacement heart valve assembly 10 within a native heart valve 2.

While this invention may be embodied in many different forms, there are described in detail herein specific embodiments. This description is an exemplification of the principles of the invention and is not intended to limit it to the particular embodiments illustrated.

For the purposes of this disclosure, like reference numerals in the figures shall refer to like features unless otherwise indicated.

With regard to FIG. 1A, in some embodiments, a replacement heart valve assembly 10 comprises a stent frame 12 and a replacement valve 14. The replacement valve 14 is attached to the stent frame 12 and, in some embodiments, has a plurality of leaflets 20. As further shown in FIG. 1A, the replacement heart valve assembly 10 is inserted into a native heart valve 2. As shown in FIG. 1A, the replacement heart valve assembly 10 is in a deployed configuration 17.

Figure 1B:
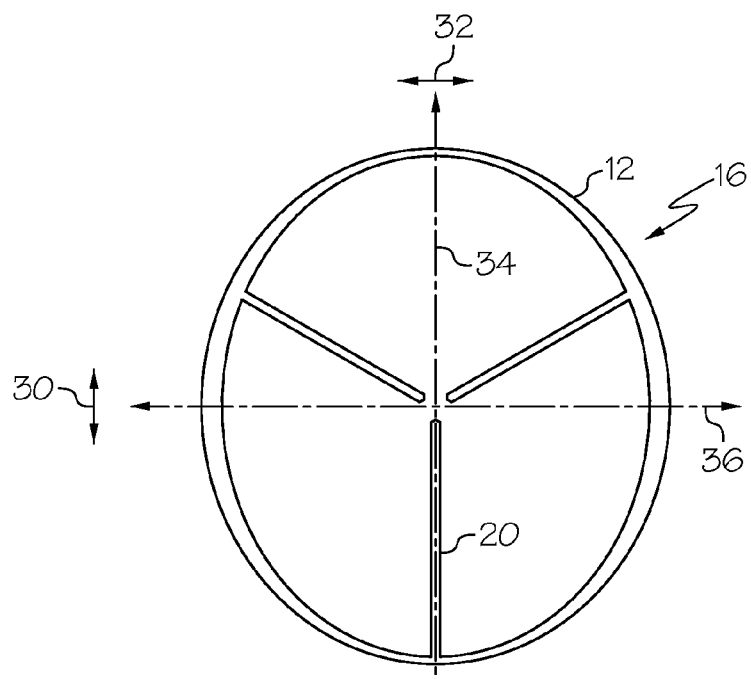
FIG. 1B shows a top view of the stent frame 12 of FIG. 1A in an unrestricted configuration 16.

Turning to FIG. 1B, the stent frame 12 of FIG. 1A is shown therein in an unrestricted configuration 16. In some embodiments, in the unrestricted configuration 16, the stent frame 12 has an oval or elliptical shape. As used herein, the phrase "unrestricted configuration" refers to a configuration in which the stent frame 12 and/or replacement heart valve assembly 10 has been expanded but does not have any outside force acting on the stent frame 12 and/or replacement heart valve assembly 10. In some embodiments, when the stent frame 12 is in the unrestricted configuration, the leaflets 20 are not in alignment.

In some embodiments, the stent frame 12 is stiffer in one direction than another. For example, in some embodiments, the stent frame 12 is stiffer in a first direction 30 than a second direction 32. Further, in some embodiments, the stent frame 12 has fewer struts along a portion thereof that is desirably less stiff and more struts along a portion thereof that is desirably stiffer.

Figure 1C:
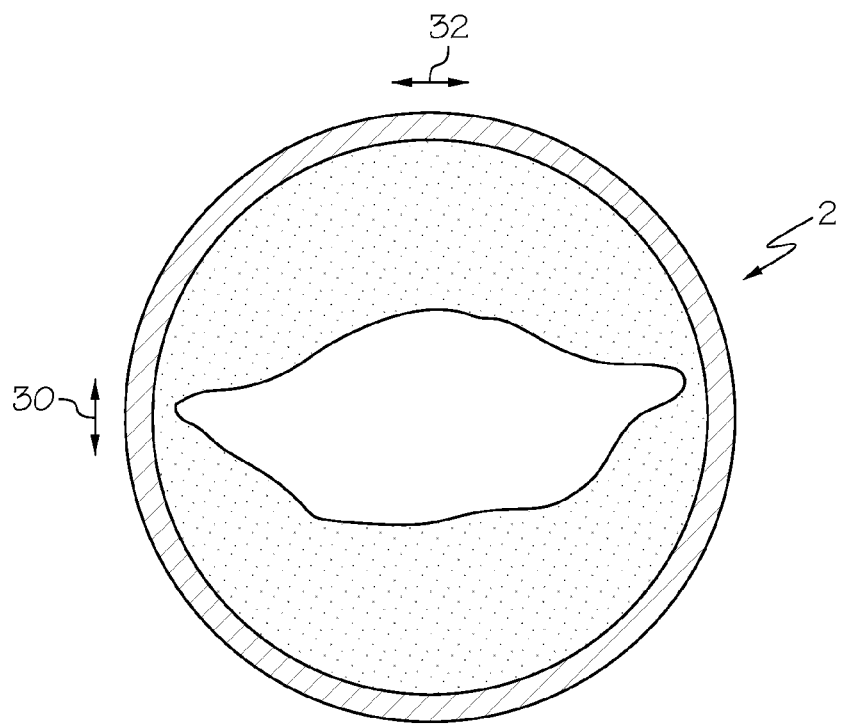
FIG. 1C shows a top view of a native heart valve 2.

When used with a stenosed or bicuspid aortic valve 2, as shown in FIG. 1C, the stent frame 12 of FIG. 1B is placed within the aortic valve such that, upon deployment, the stent frame 12 assumes a circular configuration, for example as shown in FIG. 1A. This, in turn, allows the replacement valve 14 to coapt, improving valve performance and longevity. Moreover, the stent frame 12 of FIG. 1B can, for example, be inserted into the native heart valve 2 shown in FIG. 1C so that the first direction 30 of FIG. 1B aligns with the first direction 30 shown in FIG. 1C. In this way, where the bicuspid aortic valve of FIG. 1C asserts a greater force in the first direction 30 than the second direction 32, the stent frame 12 (FIG. 1B) counteracts the applied forces to yield a circular stent frame 12, when disposed within the native aortic valve 2, shown in FIG. 1A.

As further shown in FIGS. 1A and 1B, in some embodiments, the stent frame 12 has a non-uniform thickness. In this way, the stent frame 12 is biased to be stiffer in one direction than the other. Such a structure counteracts the force applied to the stent frame 12 by a bicuspid and/or stenosed heart valve. The non-uniform thickness aids the stent frame 12 in resisting the non-uniform force applied to the stent frame 12 by the bicuspid aortic valve. Upon implantation, the resulting replacement heart valve assembly 10 takes on a circular configuration. Consequently, the leaflets 20 come together, upon closing of the replacement valve 14, to provide improved coaptation. With further regard to FIG. 1B, in some embodiments, the stent frame12 is thickest at the intersection of the minor axis 36 and thinnest at the intersection of the major axis 34. In some embodiments, the stent frame 12 is stiffer in the direction of the major axis 34 than the direction of the minor axis 36.

In some embodiments, the stent frame 12 is circular in both the deployed configuration 17 and the unrestricted configuration .16 In particular, in such an embodiment, the stent frame 12 comprises a non-uniform structure to counteract a greater force applied to the stent frame 12 in the first direction 30 than in the second direction 32.

In addition to the foregoing, in some embodiments, the stent frame 12 is stiffer in one direction than another by way of the strut configuration, strut width, or strut length. Other suitable structures can be employed to bias the stent frame 12 to counteract the forces applied by a bicuspid aortic valve and/or stenosed aortic valve. For example, the temper of the stent frame can be varied by region.

Upon introduction, in some embodiments, the stent frame 12 exerts a greater force on the diseased valve along the major axis 34, directed parallel to the first direction 30 (FIG. 1C), than it does along the minor axis 36, directed parallel to the second direction 32. Further, in some embodiments, the major axis 34 is oriented towards the greatest amount of stiff plaque.

Figure 2:
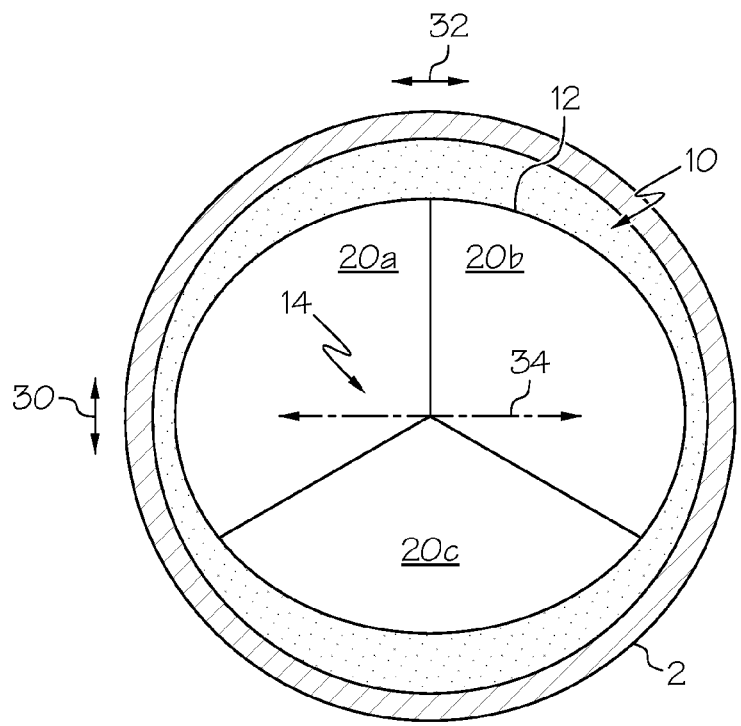
FIG. 2 shows a top view of an embodiment of a replacement heart valve assembly 10 within a native heart valve 2.

Turning to FIG. 2, in some embodiments, the stent frame 12 has an elliptical shape that is retained upon deployment into the native aortic valve 2. More particularly, in some embodiments, the stent frame 12 is oriented within the native aortic valve 2, for example a bicuspid aortic valve, such that the elliptical shape of the stent frame 12 is aligned with the oblong shape of the native aortic valve 2. Stated differently, in some embodiments, the stent frame 12 has a major axis 34 that is aligned with the second direction 32.

In some embodiments, for example as further shown in FIG. 2, the leaflets 20 are shaped to coapt when the stent frame 12 has an elliptical shape. Moreover, in some embodiments, two of the leaflets 20a and 20b are the same, while leaflet 20c has a shape different from that of leaflets 20a and 20b.

Figure 3:
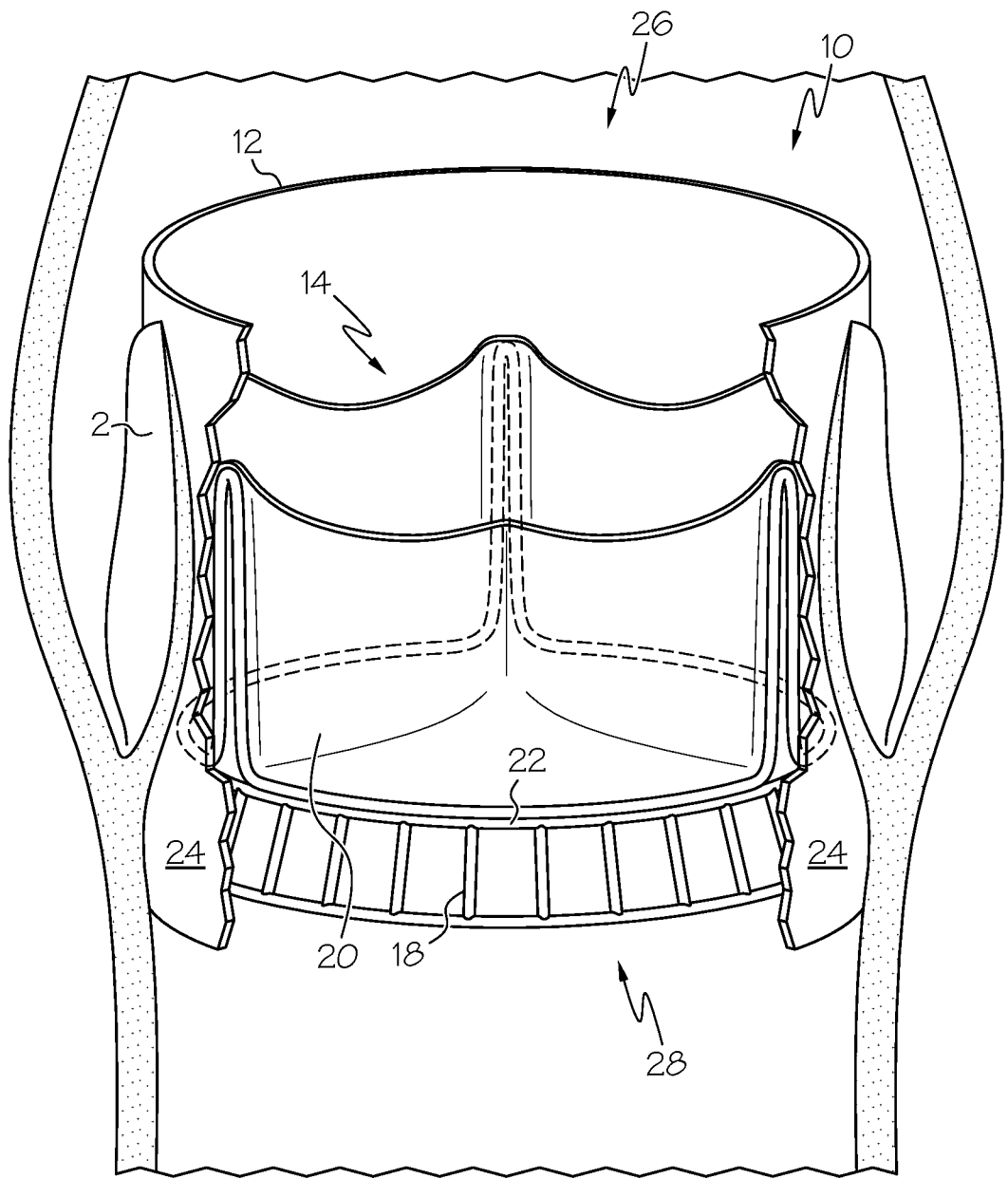
FIG. 3 shows a side view of an embodiment of a replacement heart valve assembly 10 within a native heart valve 2.

With regard to FIG. 3, in some embodiments, a replacement heart valve assembly 10 comprises a stent frame 12, a replacement valve 14, and a plurality of suspension struts 18 extending from the stent frame 12. The stent frame 12 has a proximal end 26 and an opposed distal end 28. In some embodiments, the replacement valve 14 comprises a plurality of leaflets 20 and a valve frame 22. In some embodiments, the leaflets are attached to the valve frame 22 for example by sutures. The leaflets 20 can also be attached to the valve frame 22 in other ways, for example as disclosed in U.S. Publication No. 2009/0041978; U.S. Publication No. 2009/0117334; and U.S. Publication No. 2007/0067021, each of which is herein incorporated by reference in its entirety.

In some embodiments, the suspension struts 18 extend from the stent frame 12 to the valve frame 22; in this way, the valve frame 22 is suspended within the stent frame 12 via suspension struts 18. In some embodiments, the suspension struts extend radially inwardly from the stent frame 12 and attach to the valve frame 22, which is disposed within the stent frame 12.

In some embodiments, in the deployed configuration, the stent frame 12 is elliptical and the valve frame 22 is circular. In this way, the stent frame 12 closely matches the shape of a native bicuspid aortic valve, while the valve frame 22 takes on a circular configuration to promote coaptation of the leaflets 20. Further, in some embodiments, the leaflets 20 are all the same shape.

In some embodiments, the replacement heart valve assembly 10 further comprises a sealing member 24. In some embodiments, the sealing member 24 is disposed exteriorly to the stent frame 12 to prevent leakage of blood around the stent frame 12.

In some embodiments, suspension of the replacement valve 14 within the stent frame 12 permits the replacement valve 14 to obtain a circular shape even though the stent frame 12 is somewhat elongated or elliptical. In particular, in some embodiments, the suspension struts 18 can deform upon deployment of the stent frame 12 and replacement valve 14 to allow the stent frame 12 to take on an elliptical configuration, and match the native valve geometry, while the replacement valve 14 takes on a circular configuration, to achieve the desired leaflet 20 geometry. In this way, in some embodiments, the suspension struts 18 are flexible enough to accommodate an elliptical stent frame 12 and circular replacement valve 14.

In some embodiments, the suspension struts extend from the distal end 18 of the stent frame 12. Additionally, in some embodiments, the sealing member 24 is attached to the distal end 28 of the stent frame 12. In some embodiments, at least a portion of the sealing member 24 is disposed exteriorly to the stent frame 12.

In some embodiments, the replacement heart valve assembly 10 is self-expanding. In some embodiments, however, the replacement heart valve assembly 10 is balloon expandable. Further, in some embodiments, the heart valve assembly 10 is partially self-expanding and partially balloon expandable. Further still, in some embodiments, one or more of the components of the replacement heart valve assembly 10 is self-expanding while other of the components is balloon expandable.

In some embodiments, the stent frame 12 is a slotted-tube style stent. Alternatively, in some embodiments, the stent frame 12 is formed from a woven or braided wire. In some embodiments, for example where the stent frame 12 is formed from a braided wire, it can be heat-set into an elliptical shape.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. A replacement heart valve assembly comprising:
 a stent frame;
a replacement valve, the replacement valve having a plurality of leaflets and a valve frame, the valve leaflets attached to the valve frame;
 a plurality of suspension struts attached to the stent frame and the valve frame, wherein the valve frame is suspended within the stent frame via the suspension struts; and
 a sealing member, the sealing member attached to the stent frame.

2. The replacement heart valve assembly of claim 1, wherein the replacement valve has three leaflets.

3. The replacement heart valve assembly of claim 1, wherein the stent frame has a distal end and the suspension struts are located at the distal end.

4. The replacement heart valve assembly of claim 1, wherein the suspension struts extend radially inwardly from the stent frame.

5. The replacement heart valve assembly of claim 1 having a deployed configuration, wherein, in the deployed configuration, the stent frame is elliptical and the valve frame is circular.

6. The replacement heart valve assembly of claim 1, wherein at least a portion of the sealing member is disposed exteriorly to the stent frame.

7. A replacement heart valve assembly comprising:
 a stent frame;
a replacement valve, the replacement valve having a plurality of leaflets and a valve frame, the valve leaflets attached to the valve frame;
 a plurality of suspension struts attached to the stent frame and the valve frame, wherein the valve frame is suspended within the stent frame via the suspension struts and the suspension struts extend radially inwardly from the stent frame and terminate at the valve frame; and
 a sealing member, the sealing member attached to the stent frame.

* * * * *